(12) United States Patent
Biedermann et al.

(10) Patent No.: US 7,713,292 B2
(45) Date of Patent: May 11, 2010

(54) BONE ANCHORING ELEMENT WITH THREAD THAT CAN BE UNSCREWED

(75) Inventors: Lutz Biedermann, VS-Villingen (DE); Helmar Rapp, Deiβlingen (DE)

(73) Assignee: Biedermann Motech GmbH, VS-Schwenningen (DE)

( * ) Notice: Subject to any disclaimer, the term of this patent is extended or adjusted under 35 U.S.C. 154(b) by 682 days.

(21) Appl. No.: 10/835,490

(22) Filed: Apr. 28, 2004

(65) Prior Publication Data

US 2004/0220575 A1 Nov. 4, 2004

(30) Foreign Application Priority Data

Apr. 30, 2003 (DE) .................. 103 19 781

(51) Int. Cl.
*A61B 17/88* (2006.01)
(52) U.S. Cl. ...................... 606/279; 606/316
(58) Field of Classification Search .......... 606/61, 606/72, 73, 65, 66, 300–321; 411/417, 418
See application file for complete search history.

(56) References Cited

U.S. PATENT DOCUMENTS

| | | | | |
|---|---|---|---|---|
| 264,479 | A | * | 9/1882 | Rogers ................ 411/417 |
| 383,834 | A | * | 5/1888 | Stillwell et al. .......... 411/417 |
| 1,987,474 | A | * | 1/1935 | Grant ................ 411/417 |
| 3,866,510 | A | * | 2/1975 | Eibes et al. ............ 411/418 |
| 4,693,724 | A | | 9/1987 | Rhenter et al. |
| 4,759,714 | A | | 7/1988 | Szegvary |
| 5,098,435 | A | | 3/1992 | Stednitz et al. |
| 5,338,197 | A | * | 8/1994 | Kwan .................... 433/174 |
| 5,443,467 | A | | 8/1995 | Biedermann et al. |
| 5,545,165 | A | | 8/1996 | Biedermann et al. |

(Continued)

FOREIGN PATENT DOCUMENTS

DE 42 34 118 A1 4/1994

(Continued)

OTHER PUBLICATIONS

Office Action from Japanese Patent Office for Japanese Application No. 078596/2004, mailed Sep. 1, 2009 (Translation—5 pgs.).

*Primary Examiner*—Thomas C Barrett
*Assistant Examiner*—Michael J Araj
(74) *Attorney, Agent, or Firm*—Christie, Parker & Hale, LLP

(57) ABSTRACT

A bone anchoring element (1) for anchoring an external device in a bone is described. A head (2) capable of connection to the external device is provided with a shaft (3) that can be anchored in a bone. A predetermined section of the shaft (3) has a bone thread (5). Moreover, the shaft (3) also has at least one bone thread-free surface (6,7; 11,12; 16,17; 21,22; 23) that extends from a first end to a second end of the predetermined section essentially along the direction of the shaft axis. The bone anchoring element (1), thus provided, is pressed or soft-hammered into a hole (8, 28) previously generated in the bone and fixed in the bone by rotation by a predetermined angle. If the bone anchoring element has to be removed this can be achieved by unscrewing it in the standard fashion. The disclosure also describes methods for using the bone anchoring element.

6 Claims, 5 Drawing Sheets

U.S. PATENT DOCUMENTS

| | | |
|---|---|---|
| 5,702,445 A | 12/1997 | Brånemark |
| 6,099,312 A * | 8/2000 | Alvaro ........................ 433/174 |
| 6,220,860 B1 * | 4/2001 | Hansson ..................... 433/173 |
| 6,287,311 B1 * | 9/2001 | Sherman et al. ............... 606/78 |
| 6,604,945 B1 | 8/2003 | Jones |
| 7,137,817 B2 * | 11/2006 | Mena .......................... 433/174 |
| 2002/0123752 A1 | 9/2002 | Schultheiss et al. |
| 2002/0138076 A1 | 9/2002 | Biedermann et al. |

FOREIGN PATENT DOCUMENTS

| | | |
|---|---|---|
| DE | 43 07 576 C1 | 4/1994 |
| EP | 0 714 643 A1 | 6/1996 |
| JP | 62-172944 A | 7/1987 |
| JP | 63-21506 B2 | 5/1988 |
| JP | 01-094847 A | 4/1989 |
| JP | 01-124449 A | 5/1989 |
| JP | 06-319759 A | 11/1994 |
| JP | 08-238256 A | 9/1996 |
| JP | 08-299362 A | 11/1996 |
| JP | 2610017 B2 | 2/1997 |
| JP | 10-118085 A | 5/1998 |
| JP | 2002-330976 A | 11/2002 |

* cited by examiner

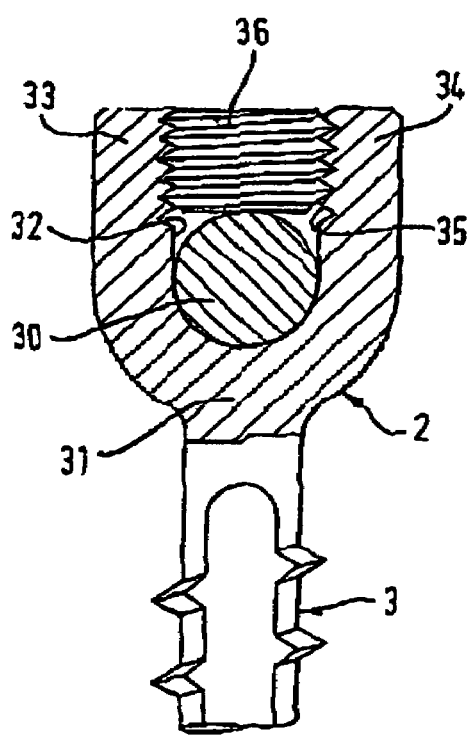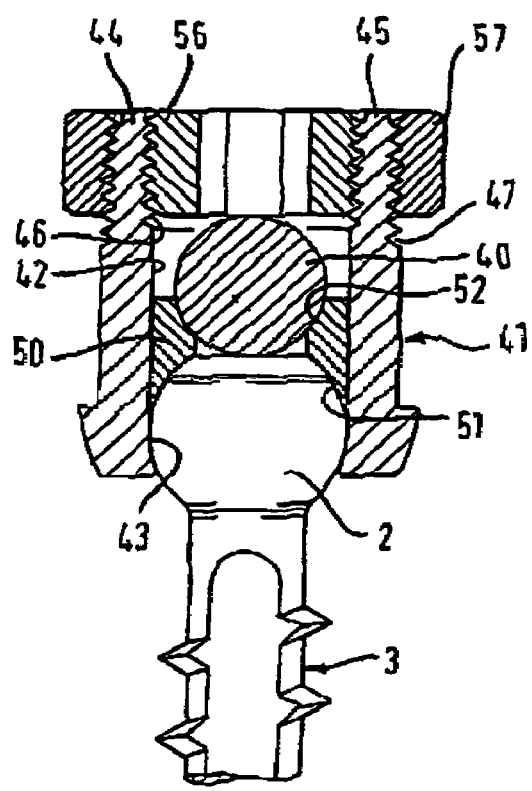

_US 7,713,292 B2_

BONE ANCHORING ELEMENT WITH THREAD THAT CAN BE UNSCREWED

FIELD OF THE INVENTION

The present invention relates to a bone anchoring element for the anchoring of a mechanical device in a bone.

BACKGROUND OF THE INVENTION

A bone anchoring element is described in DE 42 34 118 in the form of a pedicle screw. It comprises a shaft and a head that can be connected to a rod for interconnection of a plurality of pedicle screws. The shaft is provided with a thread that allows the screw to be screwed into a bone.

DE 43 07 576 describes a bone anchoring element with a polyaxial connection between the head of a bone screw and a rod.

Such bone anchoring elements are inserted into the bone by screwing-in which is a relatively time-consuming and strength-requiring process. Moreover, a classical screwing-in process may be associated with high pressure forces acting on the bone, which is undesirable in the case of older or pre-damaged bones.

For this reason, the classical process of screwing-in is less well-suited for certain clinical requirements, especially in pediatric surgery, surgery at the cervical spine, and neurosurgery.

Therefore, it is desirable to provide a bone anchoring element, in particular for use in pediatric surgery, surgery at the cervical spine, and neurosurgery, which can be inserted into the bone more rapidly, more easily, and with less force so as to avoid exerting damaging forces on the bone, while providing for secure attachment.

SUMMARY OF THE INVENTION

The present invention provides a bone anchoring element for anchoring an external device in a bone. The bone anchoring element comprises a head (2) that can be connected to the external device and a shaft (3) that can be anchored in a bone. The shaft comprises a bone thread (5) in a predetermined section and at least one bone thread-free surface (6,7; 11,12; 16,17; 21,22,23) that extends from a first end to a second end of the predetermined section essentially along the direction of the shaft axis.

By providing an area that bears no bone thread it is possible to press or insert the bone anchoring element into an attachment hole that was previously generated in the bone and then anchor the bone anchoring element by rotating it by a predetermined angle without involving a process of screwing-in. If the bone anchoring element has to be removed this can be achieved by unscrewing it in the standard fashion.

Preferred embodiments of a bone anchoring element in accord with the invention have one or more of the following features:
  the distance between the bone thread-free surface (6,7; 11,12; 16,17; 21,22,23) and the shaft axis is smaller than the distance between the crest of the bone thread (5) and the shaft axis;
  a multitude of bone thread-free surfaces (6,7; 11,12; 16,17; 21,22,23) is provided, preferably two or three;
  the multitude of bone thread-free surfaces (6,7; 11,12; 16,17; 21,22,23) are arranged at equal distances from each other in a circumferential direction;
  at least one of the bone thread-free surfaces is provided as a planar surface (6,7; 21,22,23);
  at least one of the bone thread-free surfaces (11,12) is provided to be concave in shape;
  the bone thread-free surfaces (6,7; 21,22,23) extend parallel to the shaft axis;
  the bone thread-free surfaces (16, 17) extend from the first end to the second end of the predetermined section in the form of a helical section;
  the predetermined section extends to the end of the shaft (3) that is opposite to the head (2);
  a tip (4) is provided at the end of the shaft (3) that is opposite to the head (2);
  at least one of the bone thread-free surfaces (6,7; 11,12; 16,17; 21,22,23) is roughened or coated in order to improve the in-growth of bone;
  the shaft (3) is made from a shape memory alloy;
  the head (2) is provided as receiving member (31) for connecting to a rod (30); and
  the head (2) is connected to the shaft (3) either firmly or articulated.

The invention also provides a method for using a bone anchoring element for anchoring an external device in a bone, the method comprising providing a bone anchoring element as described herein, having a first cross-sectional shape forming a hole in the bone having a second cross-section with dimensions equal to or slightly less than the dimensions of the first cross-sectional shape, inserting the bone anchoring element into the hole, and rotating the bone anchoring element around its longitudinal axis to a predetermined angle to engage the bone thread in the bone. A plurality of bone anchoring elements can be connected to a rod for stabilization of vertebrae or bones. Optionally the method includes a step of removing the bone anchoring element. The step of removing comprises a step of unscrewing the bone anchoring element in the standard fashion.

Additional features and characteristics of the present invention are evident from the description of embodiments on the basis of the attached drawings.

BRIEF DESCRIPTION OF THE DRAWINGS

FIG. 11 shows a schematic representation of a monoaxial connection between a bone anchoring element and a rod;

FIG. 12 shows a schematic representation of a polyaxial connection between a bone anchoring element and a rod;

DETAILED DESCRIPTION OF THE INVENTION

In accord with the present invention, bone anchoring elements are provided that can be inserted into a bone without screwing the threaded length of the shaft into the bone to the desired depth. A first embodiment of a bone anchoring element in accord with the present invention is described with reference to FIGS. 1 through 5.

Figure 1:
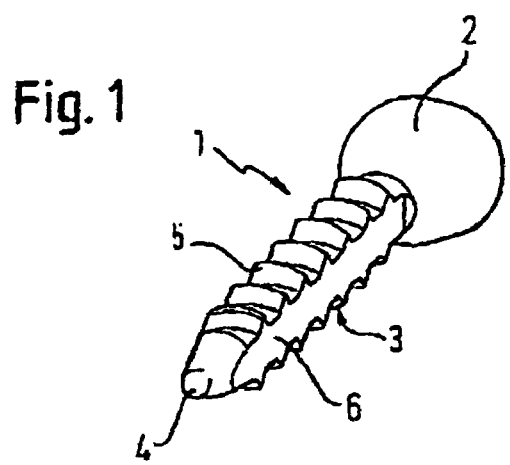
FIG. 1 shows a perspective view of a bone anchoring element according to a first embodiment of the present invention.
Figure 3:
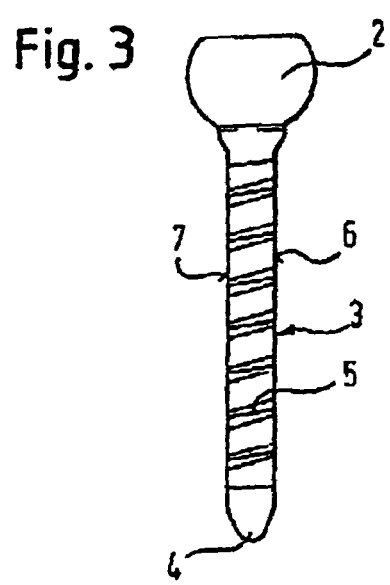
FIG. 3 shows a front elevational view of the bone anchoring element of FIG. 1 (i.e., generally in the direction of the arrow A in FIG. 2).
Figure 4:
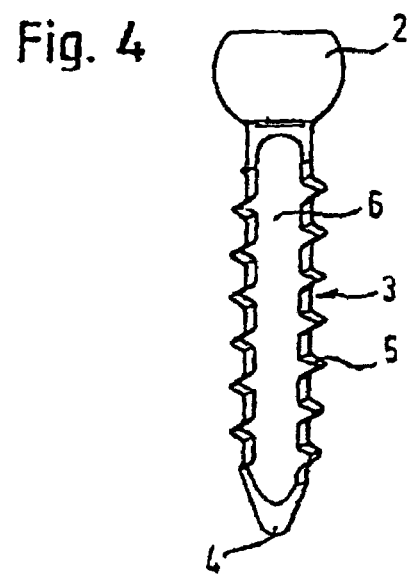
FIG. 4 shows a side elevational view of the bone anchoring element of FIG. 1 (i.e., generally in the direction of the arrow B in FIG. 2).

As is best seen in FIG. 1, the bone anchoring element 1 comprises a head 2 and a shaft 3. Head 2 is provided to be spherical segment-shaped and comprises means for engagement with a rotating tool for turning the bone anchoring element. Such means can comprise a slot, cross slot, hexagonal recess, or outer hexagonal geometry, or similar device (not shown).

The shaft 3 comprises a tip 4 at its end opposite to the head. A bone thread 5 extends over the entire length of the shaft.

Two opposite sides of the shaft 3 are provided with two planar surfaces 6, 7, which are parallel with respect to each other and to the shaft axis (longitudinal axis of shaft 3) and extend over substantially the entire length of the shaft. The distance between surfaces 6, 7 is smaller than the core diameter of bone thread 5, such that surfaces 6, 7 interrupt bone thread 5.

Figure 2:
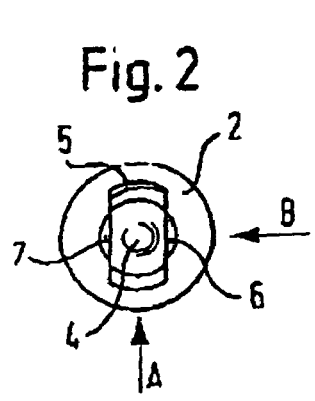
FIG. 2 shows a plan view looking at the tip of the bone anchoring element of FIG. 1.

As is best seen in FIG. 2, the cross-section of the shaft 3 thus becomes approximately rectangular, but has curved narrow sides that are formed by the thread portion. A first dimension of the cross-section is determined by the distance between surfaces 6, 7 and a second dimension orthogonal to the first direction is determined by the outer diameter of bone thread 5.

The bone anchoring element 1 typically is made of steel, titanium or any other body-compatible and sufficiently stable material.

Figure 5:
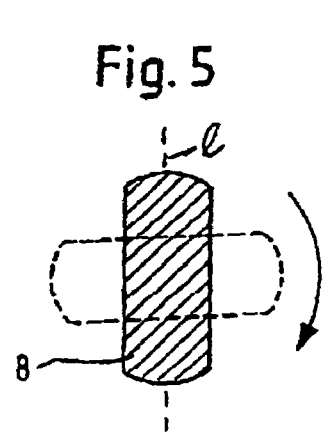
FIG. 5 shows a schematic representation of the function of the bone anchoring element according to the first embodiment.

In order to insert anchoring element 1, first a corresponding oblong hole 8 is generated in the bone, the hole having a cross-sectional shape as is best illustrated by the cross-hatched area in FIG. 5. This can be accomplished, for instance, by drilling twin holes followed by removal of the separating wall with a rasp. Alternatively, the oblong hole can be generated with a transverse cutter or profile-forming cutter. The profile of oblong hole 8 corresponds approximately to the cross-section of shaft 3. However, alternatively, it also can be slightly smaller.

Subsequently, shaft 3 of bone anchoring element 1 is inserted into oblong hole 8 by pressing or soft-hammering such that the longitudinal axis of a sectional plane of shaft 3 perpendicular to the shaft axis is approximately identical to the longitudinal axis l of oblong hole 8. In this arrangement, the bone anchoring element 1 is seated in oblong hole 8 only so firmly that it can still be removed by pulling.

Subsequently, using a rotating tool engaged onto or into the head, bone anchoring element 1 is rotated by a pre-determined angle, preferably 90° for this embodiment, as depicted by the dashed line in FIG. 5. As a result, the teeth of bone thread 5 now engage the bone and bone anchoring element 1 is firmly seated and fixed in the bone.

By rotating it further to an angle of 180° or by rotating back to the initial position, if needed, bone anchoring element 1 can be loosened and/or removed from the bone.

In the course of time, the bone grows into the empty spaces and, thus provides additional stability to bone anchoring element 1.

In certain cases, it may be necessary to remove bone anchoring element 1 from the bone after an extended period of time, when bone anchoring element 1 is firmly surrounded by bone, e.g. if the anchored device is to be removed. At this time, simply rotating the bone anchoring element 90° to its original insertion position and pulling out the element will no longer be possible. In this case, bone thread 5 serves for the purpose of allowing bone anchoring element 1 to be removed from the bone by unscrewing with a rotating tool like a conventional bone screw.

Figure 6:
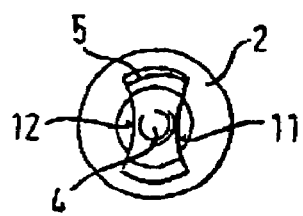
FIG. 6 shows a plan view looking at the tip of a bone anchoring element according to a second embodiment of the present invention.

FIG. 6 shows a second embodiment of a bone anchoring element in accord with the present invention. In place of planar surfaces 6, 7, as illustrated for the first embodiment, shaft 3 of bone anchoring element 1 comprises two opposite surfaces 11, 12, which are curved in the direction of the shaft axis such that the cross-section of shaft 3 has opposing concave longitudinal sides. In all other regards, the design and the use of the bone anchoring element 1 are identical to the first embodiment.

Due to the concave surfaces 11, 12 the in-growth of bony material is improved which can provide for more stability of the attachment of bone anchoring element 1 in the bone.

Figure 7:
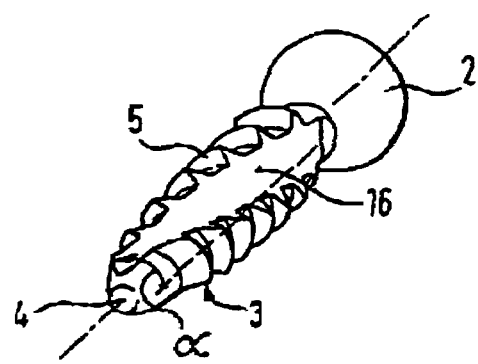
FIG. 7 shows a perspective view of a bone anchoring element according to a third embodiment of the present invention.

FIG. 7 shows a third embodiment according to the present invention. Here, in place of surfaces 6, 7 of the first embodiment or surfaces 11, 12 of the second embodiment, shaft 3 of bone anchoring element 1 comprises two opposite surfaces 16, 17 that are twisted around the shaft axis by a predetermined angle α, such that they form a helix section. In this embodiment, at any cross section of the shaft perpendicular to the shaft axis the surfaces 16, 17 will show a straight line. In all other regards, the design and the use of the bone anchoring element, 1, are identical to the first embodiment.

Although the predetermined angle α is shown in FIG. 7 as being approx. 90° for illustration purposes, the angle is preferably in the range of 90°±45°. The slight twisting of surfaces 16, 17 also improves the anchoring of bone anchoring element 1 in the bone.

Similar to surfaces 11, 12 of the second embodiment, alternatively, the surfaces 16, 17 of the third embodiment can also be concave.

Figure 8:
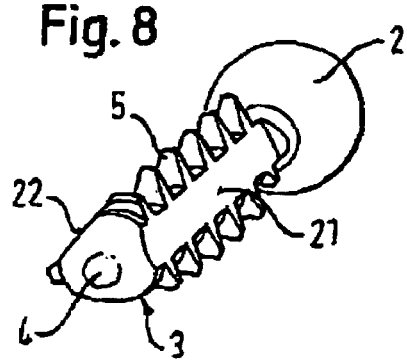
FIG. 8 shows a perspective view of a bone anchoring element according to a fourth embodiment of the present invention.
Figure 9:
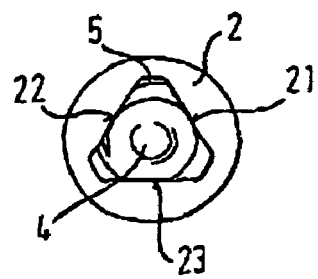
FIG. 9 shows a plan view looking at the tip of the bone anchoring element of FIG. 8.

A bone anchoring element according to a fourth embodiment according to the present invention is described with reference to FIGS. 8 through 10. In place of the two parallel surfaces 6, 7, shaft 3 of bone anchoring element 1 comprises three planar surfaces 21, 22, 23 which are off-set from each other by about 120° each, such that the cross-section of shaft 3 becomes approximately triangular. The distance between the bone thread-free surfaces, 21, 22, 23, and the shaft axis is smaller than the core radius of bone thread 5 such that surfaces 21, 22, 23 interrupt bone thread 5. In all other regards, the design and the use of the bone anchoring element, 1, are identical to the first embodiment.

Figure 10:
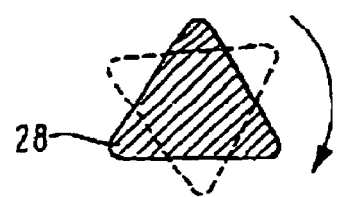
FIG. 10 shows a schematic representation of the function of the bone anchoring element according to the fourth embodiment.

In order to insert the bone anchoring element 1, according to the fourth embodiment, first a corresponding triangular hole 28 is generated in the bone, as is best seen in FIG. 10 where it is illustrated by the cross hatched area. This can be accomplished for instance by drilling a hole followed by shaping with a rasp. Alternatively, triangular hole 28 can also be generated with a transverse cutter or profile-forming cutter. The cross-section of triangular hole 28 corresponds approximately to the cross-section of shaft 3 or is slightly smaller than the cross-section.

Subsequently, shaft 3 of bone anchoring element 1 is inserted into triangular hole 28 by pressing or soft-hammering such that the triangular sides of the cross-section through shaft 3 correspond approximately to the triangular sides of triangular hole 28. In this arrangement, the bone anchoring element 1 is seated in triangular hole 28 firmly to such an extent that it can still be removed by pulling.

Subsequently, bone anchoring element 1 is rotated by a rotating tool engaging on or in the head by a pre-determined angle, preferably 60° (depicted by the dashed line in FIG. 10). As a result, the teeth of bone thread 5 engage the bone and bone anchoring element 1 attains a firm seat.

By rotating further to an angle of 120° or rotating back to the initial position, bone anchoring element 1 can be loosened, if needed, and removed from the bone.

As discussed above, bone anchoring element 1 of the fourth embodiment can be removed from the bone after an extended period of time, when it is firmly surrounded by bone, by unscrewing it with a rotating tool much like a conventional bone screw.

Similar to surfaces 11, 12 of the second embodiment, surfaces 21, 22, 23 of the fourth embodiment also can be provided to be concave in shape and/or twisted with respect to each other like surfaces 16, 17 of the third embodiment.

The bone anchoring element of the invention, such as described in the first four embodiments, is ideally suited for the insertion into the pedicle of a vertebral bone, but also is suited for all other bones in which a mechanical device is to be anchored. Two types of a connection between a bone anchoring element and a rod are described in the following as examples for a connection of the bone anchoring element to an external device.

FIG. 11 is a schematic representation of a monoaxial connection between a bone anchoring element 1 and a rod 30.

As is well known to those skilled in the art, the head 2 of bone anchoring element 1 is provided as the receiving member 31 for rod 30 and comprises a U-shaped recess 32 by which two free legs 33, 34 are formed. The width of U-shaped recess 32 corresponds approximately to the diameter of rod 30. An internal thread 35 is provided on the inside of free legs 33, 34.

After the insertion of bone anchoring element 1 into the bone, rod 30 is inserted into U-shaped recess 32. Subsequently, a screw 36 is screwed into internal thread 35 far enough for rod 30 to be fixed between screw 36 and the base of U-shaped recess 32.

Any other type of monoaxial connection between shaft 3 and the receiving member known to those skilled in the art is also useful in the practice of the present invention. Moreover, the design of the receiving member for the rod is not limited to the embodiment shown. For instance, in one modification, the receiving member does not comprise an internal thread. In this case, the receiving member is connected to a threaded rod and fixed by nuts engaging on the sides. Again, any receiving member design known to those skilled in the art is useful in the practice of the present invention.

FIG. 12 is a schematic representation of a polyaxial connection between a bone anchoring element 1 and a rod 40.

To provide for the connection, an essentially cylinder-shaped receiving member 41 with a longitudinal bore 42 is provided. As is well known to those skilled in the art, the diameter of longitudinal bore 42 is slightly larger than that of the spherical segment-shaped head 2 of bone anchoring element 1. Longitudinal bore 42 extends from a first end of receiving member 41 to a second end opposite to the first end. A spherical segment-shaped section 43, with a diameter of the shape that is approximately identical to that of spherical segment-shaped head 2 of bone anchoring element 1, is provided between the second end of receiving member 41 and longitudinal bore 42.

In addition, receiving member 41 comprises a U-shaped recess (not shown), whose width corresponds approximately to the diameter of rod 40. This U-shaped recess forms two legs 44, 45 in receiving member 41. The inside of the legs 44, 45 is provided with an internal thread 46 and the outside with an external thread 47.

In addition, a sleeve-shaped pressure element 50 is provided. At one end of sleeve-shaped pressure element 50 a spherical segment-shaped recess 51 is provided which has approximately the same diameter of the sphere as spherical segment-shaped head 2 of bone anchoring element 1, and at the other end a cylinder segment-shaped recess 52 is provided which has approximately the same diameter as rod 40.

Moreover, for the purpose of fixing the rod and the head, an internal screw 56, which can be screwed into internal thread 46, and a nut 57, which can be screwed onto external thread 47, are provided.

In operation, shaft 3 of bone anchoring element 1 is inserted into receiving member 41 proceeding from the first end of receiving member 41 until head 2 of bone anchoring element 1 is held within spherical segment-shaped section 43. Subsequently, bone anchoring element 1 is introduced into the bone. For this purpose, bone anchoring element 1 is pressed or hammered into a hole in the bone that was previously generated, as described above.

Subsequently, the bone anchoring element 1 is rotated by a rotating tool an appropriate amount to fix it in the bone and proceeding from the first end of receiving member 41 sleeve-shaped pressure element 50 is slid into longitudinal bore 42 such that spherical segment-shaped recess 51 comes to rest on head 2 of bone anchoring element 1. Then rod 30 is inserted into the U-shaped recess such that it comes to rest in cylinder-segment shaped recess 52 of pressure element 50.

Alternatively, receiving member and sleeve-shaped pressure element 50 are preassembled and anchoring element 1 is rotated by a rotating tool, which is guided through a coaxial bore in sleeve-shaped pressure element 50.

Subsequently, screw 56 is screwed into internal thread 46 such that head 2 of bone anchoring element 1 is fixed by pressure element 50 and, simultaneously, rod 40 is fixed by screw 56. Finally, nut 57 is screwed onto external thread 47 to secure the fixation.

The polyaxial connection between the head and the receiving member described above is presented only as an example. Again, any receiving member and polyaxial connection design known to those skilled in the art is useful in the practice of the present invention. The section 43 of the receiving member can be of a shape other than a spherical segment, for example otherwise rounded or conical.

The spherical segment-shaped head illustrated in the first through fourth embodiment is particularly well-suited for the polyaxial connection between the bone anchoring element and the external device described above. However, the bone anchoring element can be provided with a head of any other shape that allows the external device to be anchored to be connected and/or fixed in a monoaxial or polyaxial fashion. This includes, for example, the provision of a simple countersunk or fillister head for fixing a plate to a bone.

Alternatively, the shaft of the bone anchoring element can be without tip. Moreover, it can be slightly conical in shape to ease its insertion into the bone.

The thread can extend only over a predetermined longitudinal section of the shaft rather than over the entire length of the shaft.

The number of bone thread-free surfaces is not limited to two or three. Alternatively, only one surface, or any number of surfaces greater than three, can be provided. The number is limited only by the size of circumference of the shaft.

The distance of the surfaces from the shaft axis does not necessarily have to be smaller than the core radius of bone thread 5. It can also be selected to be identical to or larger than the core radius. In any case, though, is has to be smaller than the distance between the crest of the bone thread and the shaft axis.

The surfaces corresponding to concave surfaces 11, 12 do not have to be curved across their entire width. It is sufficient if merely a part of the surface is curved. Alternatively, there can be a v-shaped groove in the surface or any other geometric configuration that provides for additional bone growth around the shaft.

In order to improve the in-growth of bone, the surfaces can be roughened and/or coated, e.g. with hydroxyapatite.

Moreover, the bone anchoring element can be provided with a longitudinal bore which extends through its head and is open or closed at the tip, and bores which branch off from the longitudinal bore in a lateral direction and open on the lateral walls of the shaft, said bores allowing for a medication or bone cement to be injected into the attachment bore.

In a further embodiment, the bone anchoring element can be made from a shape memory alloy, e.g., Nitinol™. In this case, the bone anchoring element may be provided, e.g., such that, at room temperature, it assumes the shape corresponding to FIG. 1, in which the bone thread-free surfaces are planar and parallel to each other, and, at body temperature, assumes the shape corresponding to FIG. 7, in which the surfaces are twisted with respect to each other.

During insertion at room temperature, the parallel surfaces allow for easy insertion of the bone anchoring element. Once inside the body, the shape of the bone anchoring element changes such that the surfaces become twisted and additional stability in the bone can be achieved.

The bone anchoring element made from the shape memory alloy also can be formed such that the teeth of the bone thread are smaller at room temperature than at body temperature. As a result, the teeth of the bone thread grow once they are inside the body such that additional stability in the bone can be achieved.

Figure 13:
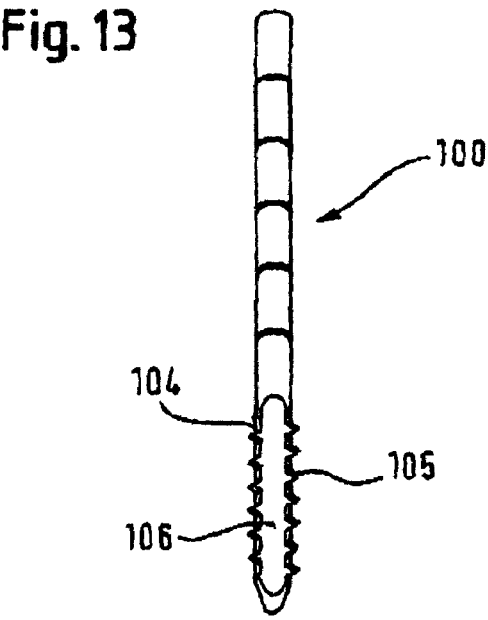
FIG. 13 shows a second embodiment of the invention.

In a second embodiment shown in FIG. 13 the bone anchoring element 100 comprises a shaft, but lacks a head. The shaft has a section 104 which is formed like the shaft 3 of the bone anchoring elements of the previously described embodiments with bone thread sections 105 and bone thread-free sections 106. Adjacent to section 103 the bone anchoring element comprises a cylindrical section without bone thread. Such bone anchoring element is used e.g. in place of a usual Schanz screw or pin screw.

Figure 14:
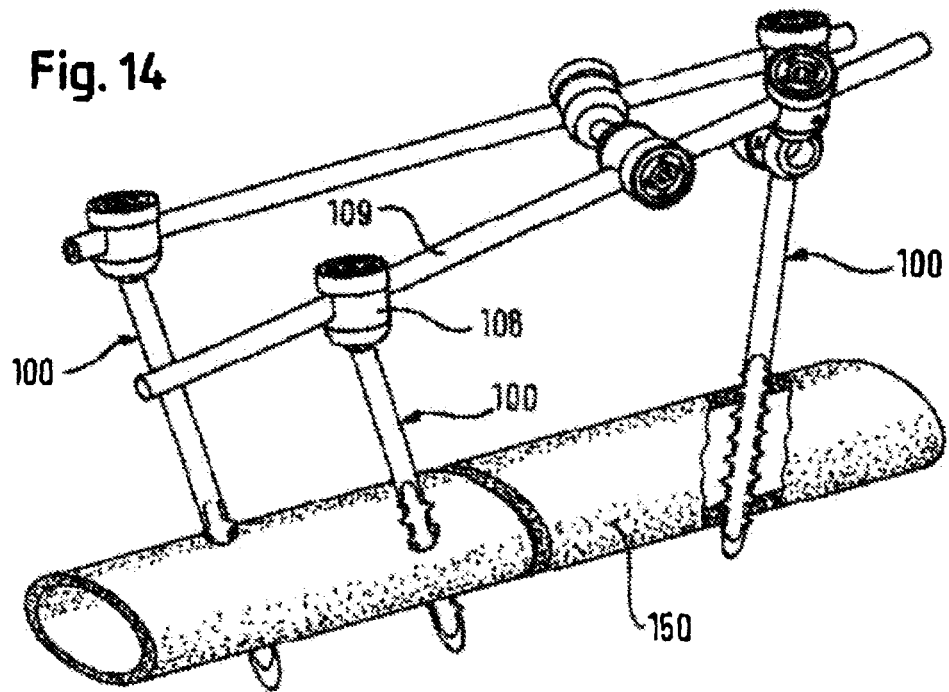
FIG. 14 shows a third embodiment of the invention.

FIG. 14 shows an example of application of the bone anchoring element 100 in a Fixateur externe to be used for example for stabilizing fractures of long bones 150. The bone anchoring element is anchored with section 103 in the long bone and connected to a receiving element 108 for receiving a rod 109.

Figure 15:
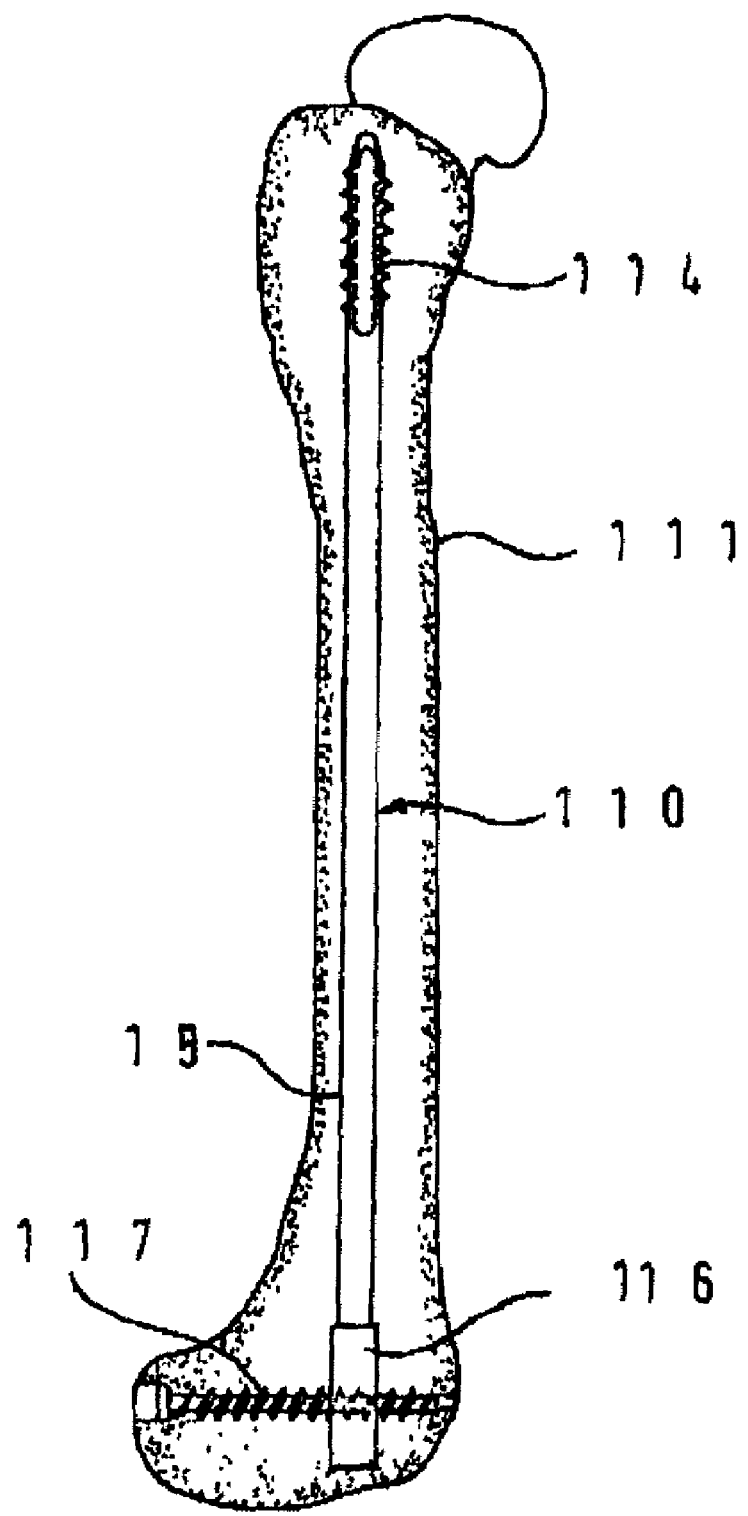
FIG. 15 shows a further example of application of the bone anchoring element according to the invention.

In a third embodiment shown in FIG. 15 the bone anchoring element 110 is formed as a marrow nail to be anchored in a long bone 111 such as femur or humerus. The bone anchoring element comprises a shaft having a section 114 which is formed like the shaft 3 of the bone anchoring elements of the first and second embodiment with bone thread sections and bone thread-free sections. The shaft further has a bone thread free section 115 and a section 116 through which a bone screw 117 is screwed for fixation. In the example shown there is no external device to be connected.

The invention has been described in detail, including the preferred embodiments thereof. However, it will be appreciated that those skilled in the art may make modifications and improvements within the spirit and scope of the invention.

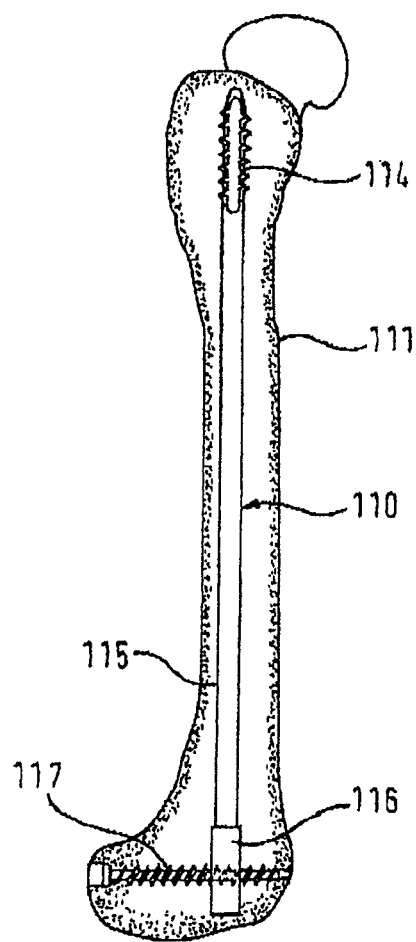

What is claimed is:

1. A method for using a bone anchoring element for anchoring an external device in a bone, the method comprising:
providing a bone anchoring element comprising:
a head section that can be connected to the external device; and
a shaft, which can be anchored in the bone and is connected to the head section, having a longitudinal axis;
the shaft comprising:
a bone thread on a predetermined section of the shaft, the bone thread having a crest and a first end and a second end spaced apart longitudinally along the shaft, and
at least one bone thread-free surface that extends along the direction of the shaft axis from the first end to the second end of the bone thread,
wherein the bone anchoring element comprises a first cross-sectional shape; forming a hole in the bone having a second cross-section with a shape corresponding to that of the first cross-section and with dimensions equal to or slightly less than the dimensions of the first cross-sectional shape;
inserting the bone anchoring element into the hole without screwing the bone anchoring element into the hole; and
rotating the bone anchoring element around its longitudinal axis to a predetermined angle to engage the bone thread in the bone.

2. The method according to claim 1, wherein the step of forming a hole comprises drilling a hole and removing bone material with a rasp to obtain the desired cross-sectional shape.

3. The method according to claim 1, wherein the step of forming a hole comprises cuffing the bone with a transverse cutter or with a profile-forming cutter.

4. The method according to claim 1, wherein the head section comprises a receiving member for connecting to a rod and the method further comprises connecting the receiving member to a rod.

5. The method of claim 4, wherein the method further comprises repeating the steps for a plurality of bone anchoring elements and connecting the plurality of bone anchoring elements with the rod.

6. The method of claim 1, further comprising a step of removing the bone anchoring element by unscrewing it.

* * * * *

UNITED STATES PATENT AND TRADEMARK OFFICE
CERTIFICATE OF CORRECTION

| | | |
|---|---|---|
| PATENT NO. | : 7,713,292 B2 | Page 1 of 2 |
| APPLICATION NO. | : 10/835490 | |
| DATED | : May 11, 2010 | |
| INVENTOR(S) | : Lutz Biedermann et al. | |

It is certified that error appears in the above-identified patent and that said Letters Patent is hereby corrected as shown below:

In the Drawings

FIG. 15, Sheet 5 of 5       Delete Drawing Sheet 5 and substitute therefore the Drawing Sheet, consisting of FIG. 15, as shown on the attached page Column 7, line 11           Delete "is" Insert -- it --

Column 8, Claim 3, line 47  Delete "cuffing" Insert -- cutting --

Signed and Sealed this
Twenty-eighth Day of June, 2011

David J. Kappos
*Director of the United States Patent and Trademark Office*